United States Patent [19]

Hommann

[11] Patent Number: 5,504,960
[45] Date of Patent: Apr. 9, 1996

[54] ELECTRIC TOOTHBRUSH

[75] Inventor: Edgar Hommann, Grossaffoltern, Switzerland

[73] Assignee: Bausch & Lomb Incorporated, Rochester, N.Y.

[21] Appl. No.: 440,163

[22] Filed: May 12, 1995

Related U.S. Application Data

[62] Division of Ser. No. 138,787, Oct. 19, 1993, Pat. No. 5,442,827.

[51] Int. Cl.⁶ .................... A61C 17/34; A46B 13/02
[52] U.S. Cl. ................................. 15/22.1; 74/22 R
[58] Field of Search ............................ 15/22.1, 22.2, 15/22.4; 74/22 R; 433/216

[56] References Cited

U.S. PATENT DOCUMENTS

| | | | |
|---|---|---|---|
| 4,156,620 | 5/1979 | Clemens | 15/22.1 |
| 4,603,448 | 8/1986 | Middleton et al. | 15/22.1 |
| 4,989,287 | 2/1991 | Scherer | 15/22.1 |
| 5,020,179 | 6/1991 | Scherer | 15/22.1 |
| 5,077,855 | 1/1992 | Ambasz | 15/22.1 |

FOREIGN PATENT DOCUMENTS

| | | | |
|---|---|---|---|
| 0357863 | 3/1990 | European Pat. Off. | |
| 3544256 | 6/1987 | Germany | 15/22.1 |
| 8911427 | 11/1989 | Germany | |
| 3931982 | 4/1991 | Germany | 15/22.1 |

Primary Examiner—Edward L. Roberts, Jr.
Attorney, Agent, or Firm—Katherine McGuire

[57] ABSTRACT

A handle component (1) of an electric toothbrush protrudes from the end of a hollow shaft (3), which holds a drive shaft (9) coaxially therein. A brush attachment (4) with rotatable bristle tufts (6) is disposed on the hollow shaft (3) in such a way that the drive shaft (9) is coupled with a shaft (7) in the brush attachment (4), wherein said shaft (7) drives the bristle tufts (6). The hollow shaft (3) is driven by a motor to oscillate around its longitudinal axis and to slide back and forth in the direction of its longitudinal axis.

4 Claims, 2 Drawing Sheets

ELECTRIC TOOTHBRUSH

CROSS-REFERENCE TO RELATED APPLICATION

This application is a division of U.S. Ser. No. 08/138,787, filed Oct. 19, 1993, now U.S. Pat. No. 5,442,827.

BACKGROUND OF THE INVENTION

The invention relates to an electric toothbrush with a hand-held handle component, with a motor and drive mechanism, and a brush attachment, which has several rotatable tufts of bristles, fastened to said handle component. Said tufts are driven by a transmission built into said brush attachment. The drive mechanism is designed in such a way that, in addition to a rotational movement of the bristle tufts, it also creates an oscillating movement of the brush attachment about its longitudinal axis.

Such a toothbrush is the subject of U.S. Pat. No. 4,989,287 which issued on Feb. 5, 1991 and is of common ownership with the present application, and which is incorporated herein by reference. In this known toothbrush, the brush attachment can be oscillated about its longitudinal axis by means of a secure coupling link with which it is attached to the forward part of the handle component's casing. The transmission mechanism is designed as a non-rotating connecting rod within the brush attachment, wherein said connecting rod can create an oscillating movement about its longitudinal axis and a back-and-forth movement in the direction of its longitudinal axis by means of an oscillating crank and an eccentric that engages said crank. The back-and-forth movement of the connecting rod is transformed in the bristle head of the brush attachment to a rotational movement of the bristle tufts while the oscillating movement of the connecting rod creates a corresponding oscillation of the entire brush attachment.

Movement of the bristle tufts by means of a connecting rod is relatively expensive, and the connecting rod presents a problem if one wants to increase the angle at which the individual bristle tufts oscillate. Further, it is impossible to continuously rotate the bristle tufts in one rotational direction using a connecting rod.

Electric toothbrushes have also become known in which the bristle tufts are driven by a shaft instead of a connecting rod. US-A-2 215 031 and DE-A-34 06 112 are examples of this state of the art. However, in both of these toothbrushes, the part that holds the bristle tufts of the toothbrush cannot be moved by the motor of the toothbrush relative to the handle component.

OBJECTS AND ADVANTAGES

The invention addresses the problem of designing a toothbrush of the type mentioned above wherein the bristle tufts can oscillate over a large angle or even complete a full rotation, and wherein the entire brush attachment that holds the bristle tufts can be moved by a motion relative to the handle component.

SUMMARY OF THE INVENTION

The invention solves this problem by designing the transmission mechanism which moves the bristle tufts of the brush head as a revolving shaft, while the brush attachment is designed to be removably fixed to a hollow shaft that can rotate and/or slide within the handle component. A drive shaft, which is located within said hollow shaft, is driven by a drive mechanism and removably couples with the shaft in the brush attachment. The drive mechanism is operable to simultaneously rotate the drive shaft and create an oscillating movement of the hollow shaft around its longitudinal axis and a back-and-forth movement in the direction of its longitudinal axis.

Since, according to the invention, the brush attachment is not inserted into the casing but onto a hollow shaft, and since the drive shaft for the shaft of the brush attachment is placed inside the hollow shaft, the brush attachment can be moved by driving the hollow shaft, without thereby affecting the drive of the bristle tufts. The toothbrush of the invention can be assembled relatively simply, and the movement of the brush attachment cleans teeth better than an electric toothbrush in which only the bristle tufts rotate. Driving the bristle tufts with a shaft makes it possible for said bristle tufts to rotate either continuously or to oscillate back and forth over a large angle.

The mechanism for moving the hollow shaft and the drive shaft can be designed in different ways. A particularly simple solution is provided in which the hollow shaft is arranged to be rotatable and axially movable, the drive mechanism has a toothed wheel, designed as a bevel or contrate gear, which is driven by the pinion of the motor. The toothed wheel turns, perpendicularly to the main extension of the handle component, around the central axis of the bevel gear. The toothed wheel engages with an eccentric pin, which is aligned in parallel to its central axle, and a notch of an oscillating crank, which is connected to said hollow shaft parallel to the axis. The toothed wheel, which is designed as a bevel wheel or contrate gear, on the side that lies opposite to the side of the pinion of the motor, meshes with a pinion of the drive shaft.

In such a toothbrush, the individual tufts of bristles may rotate continuously in one direction. The design of the mechanism in the brush attachment can be such that, for instance, the bristle tufts on one side rotate in the opposite direction to those on the other side. Simultaneously with the rotational motion of the bristle tufts, the brush attachment executes an elliptical movement because of the axially sliding and simultaneous oscillating movement of the hollow shaft around its longitudinal axis. Such a design is very advantageous for the teeth-cleaning process.

The combined movement of the hollow shaft and the drive shaft can be achieved easily by placing a crosshead, which can rotate on the eccentric pin, into the notch of the oscillating crank, and by designing the two sides of the crosshead which are parallel to the longitudinal axis of the toothbrush and/or the two corresponding sides of the notch to be curved or canted to allow the oscillating crank to perform a rocking motion. Such a mechanism corresponds largely to the previously mentioned '287 patent but differs from it, aside from its hollow shaft, primarily in that the toothed wheel with the eccentric simultaneously drives the drive shaft within the hollow shaft.

DETAILED DESCRIPTION

Figure 1:
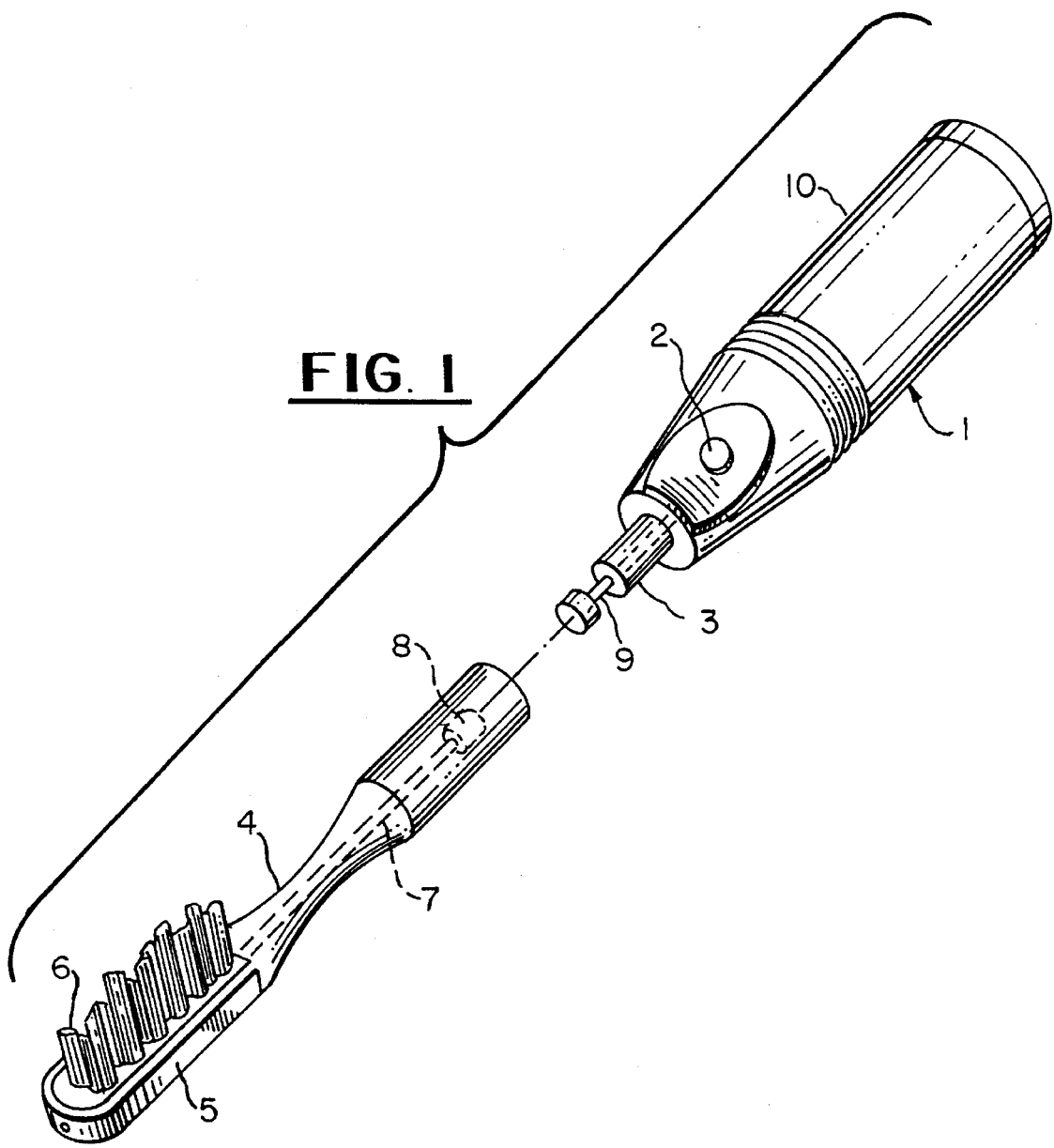
FIG. 1 is a perspective view of a partly unassembled toothbrush according to the invention.

FIG. 1 shows in perspective a still unassembled electric toothbrush with a hand-held handle component 1 having a switch 2 to turn the electric toothbrush on and off. A hollow shaft 3 protrudes from the handle component 1 over which the brush attachment 4 is placed. When attached, the brush attachment is securely held on the hollow shaft 3 by a locking device (not shown).

The brush attachment 4 has a bristle head 5 with several rotatable bristle tufts 6. To drive the bristle tufts 6, a revolving shaft 7 is disposed within the brush attachment (shown by broken lines). Shaft 7 can be coupled to a drive shaft 9 by a coupler 8 which is arranged coaxially with the hollow shaft 3 in the handle component 1.

The drive shaft 9 extends freely and coaxially within the hollow shaft 3, and is made to rotate continuously by the drive mechanism described below. Consequently, the bristle tufts 6 may either rotate in one direction or oscillate back and forth depending on the type of transmission mechanism used in the brush head (not shown herein). The hollow shaft 3 is driven in such a way that it oscillates around its longitudinal axis while simultaneously sliding back and forth in the direction of its longitudinal axis.

Figure 2:
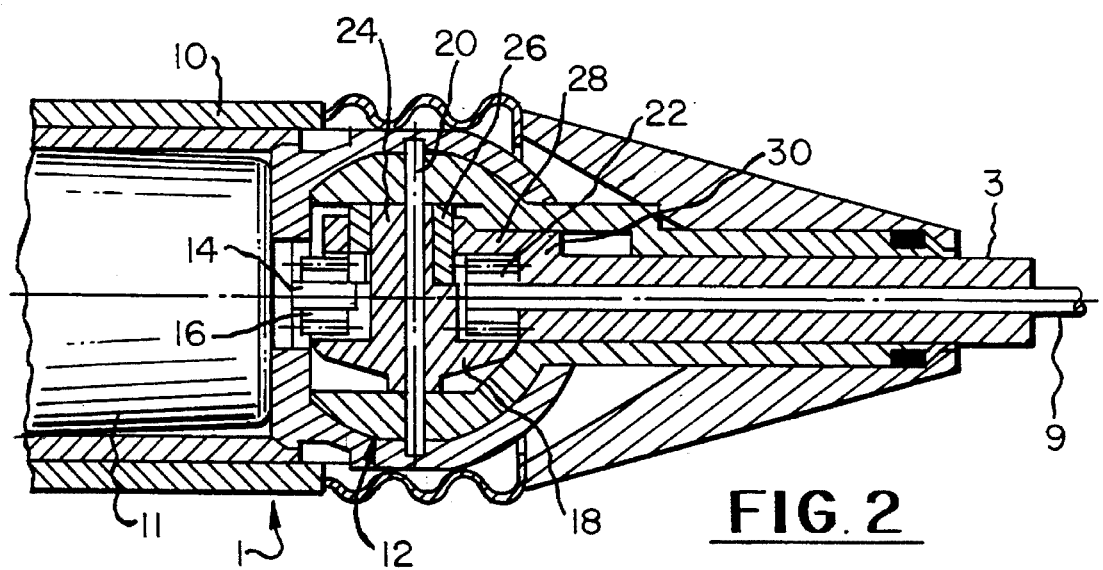
FIG. 2 is a longitudinal, cross-sectional view through an area of the transmission mechanism of the handle component of the toothbrush.

FIG. 2 shows the hollow shaft 3 and the drive shaft 9 which are driven by the motor 11. The motor 11 in turn has a motor shaft 14 with a pinion 16. Pinion 16 continuously drives a toothed wheel 18 mounted rotatably around a rigid-casing axle 20. Toothed wheel 18 may be designed as a bevel gear or contrate gear. Axle 20 is rigidly mounted to the casing and aligned perpendicular to the longitudinal axis of the handle component 1. Toothed wheel 18, on the side that lies opposite to the side of motor pinion 16, meshes with the second pinion 22, which drives the drive shaft 9. In this manner the drive shaft 9 rotates constantly in one direction.

An eccentric pin 24 is provided on the toothed wheel 26, extending in the direction of the axle 20, which engages a crosshead 26 of an oscillating crank 28. The oscillating crank 28 lies parallel to the hollow shaft 3 and is firmly connected thereto by a radial connecting link 30. The exact design of this component of the mechanism 12, including the toothed wheel 18, the eccentric pin 24, the crosshead 26 and the oscillating crank 28, is described in the '287 patent disclosure.

The hollow shaft 3 in the design shown in FIG. 2 is mounted in the casing 10 of the handle component 1 in such a way that it is rotatable and axially movable. Through the rotation of the eccentric pin 24, the hollow shaft 3 first slides back and forth in the direction of its longitudinal axis. However, since the eccentric pin 24 is mounted perpendicular to the hollow shaft 3 and since the hollow shaft 3 cannot move laterally, the oscillating crank 28 follows the lateral movement of the eccentric pin 24 by tilting around the longitudinal axis of the hollow shaft 3. This movement is also described in detail in the '287 patent disclosure. Thus, the hollow shaft 3 in this design executes a back and forth movement in longitudinal direction and also an oscillating movement around its longitudinal axis.

What is claimed is:

1. An electric toothbrush comprising:

a) a hand-held handle component having a longitudinal axis and containing a motor having a rotating motor shaft and motor shaft pinion, said handle component further including an inner drive shaft telescopingly and coaxially positioned within an outer hollow shaft, said inner and outer shafts extending exteriorly from said handle component;

b) a brush attachment for removable connection to said handle component, said brush attachment having an outer casing and a bristle head with at least one bristle tuft movably engaged by a rotatable brush head shaft extending within said outer casing;

c) means coupling said outer casing and said brush head shaft of said brush attachment to said outer hollow shaft and said inner drive shaft of said handle component, respectively, upon removably connecting said brush attachment to said handle component;

d) a bevel gear axially rotatable about a pivot pin located within said handle component transversely to a longitudinal direction of said drive shaft, said motor shaft pinion meshing with a first side of said bevel gear for rotating said bevel gear about said pivot pin;

e) an eccentric pin fixedly attached to and extending from said bevel gear in a direction parallel to said pivot pin;

f) a second pinion gear fixedly secured to the end of said inner shaft located interiorly of said handle component opposite said connection to said brush head shaft of said brush head attachment, said second pinion meshing with a second side of said bevel gear opposite said first side thereof whereby rotation of said bevel gear causes a corresponding rotation of said inner shaft, said brush head shaft and said at least one bristle tuft; and g) motion translating means for translating the rotational movement of said bevel gear to an elliptical movement of said hollow shaft and said brush attachment outer casing to which said hollow shaft removably couples, said motion translating means connected to said hollow shaft and engaging said eccentric pin of said bevel gear.

2. The electric toothbrush of claim 1 wherein said motion translating means comprises an oscillating crank extending parallel to said hollow shaft and connected thereto by a radial connecting link, said oscillating crank including an opening wherethrough said eccentric pin extends.

3. The electric toothbrush of claim 2 wherein said motion translating means further comprises a crosshead positioned within said opening, said crosshead having a central bore wherethrough said eccentric pin rotatably extends, whereby a longitudinal movement of said crosshead causes a corresponding longitudinal movement of said oscillating crank.

4. The electric toothbrush of claim 3 wherein said crosshead has two opposed lateral faces each parallel to a longitudinal axis of said hollow shaft, said two opposed faces being arc-shaped and contacting an inner portion of said opening of said oscillating crank, whereby a transverse movement of said crosshead causes a rotation of said oscillating crank about a longitudinal axis of said hollow shaft.

* * * * *